United States Patent
Vandendaele et al.

(10) Patent No.: US 10,479,963 B2
(45) Date of Patent: Nov. 19, 2019

(54) MICROCAPSULES CONTAINING MICROORGANISMS

(75) Inventors: Patrice Vandendaele, Ronse (BE); Robin Temmerman, Lokeren (BE)

(73) Assignee: Devan Chemicals NV, Ronse-Renaix (BE)

( * ) Notice: Subject to any disclaimer, the term of this patent is extended or adjusted under 35 U.S.C. 154(b) by 0 days.

(21) Appl. No.: 13/377,101

(22) PCT Filed: Jun. 7, 2010

(86) PCT No.: PCT/EP2010/003377
§ 371 (c)(1),
(2), (4) Date: Dec. 8, 2011

(87) PCT Pub. No.: WO2010/142401
PCT Pub. Date: Dec. 16, 2010

(65) Prior Publication Data
US 2012/0076864 A1     Mar. 29, 2012

(30) Foreign Application Priority Data

Jun. 9, 2009   (GB) ................................. 09099909.4

(51) Int. Cl.
| B05D 7/00 | (2006.01) |
| B05D 3/00 | (2006.01) |
| A01N 63/04 | (2006.01) |
| A01P 1/00 | (2006.01) |
| A01N 25/28 | (2006.01) |
| A01N 63/00 | (2006.01) |
| C11D 17/00 | (2006.01) |
| C11D 3/38 | (2006.01) |

(52) U.S. Cl.
CPC .......... *C11D 17/0039* (2013.01); *A01N 25/28* (2013.01); *C11D 3/381* (2013.01)

(58) Field of Classification Search
None
See application file for complete search history.

(56) References Cited

U.S. PATENT DOCUMENTS

| 6,537,583 | B1 | 3/2003 | Dupuis et al. |
| 6,652,867 | B1 * | 11/2003 | Vincent et al. ............... 424/401 |
| 8,747,999 | B2 | 6/2014 | Grey et al. |
| 2002/0164777 | A1 | 11/2002 | Kelly et al. |
| 2003/0068347 | A1 | 4/2003 | Baschong et al. |
| 2003/0126688 | A1 | 7/2003 | Peters et al. |
| 2004/0022990 | A1 | 2/2004 | Sitabkhan |
| 2006/0188582 | A1 | 8/2006 | Naylor Da Rocha Gomes |
| 2007/0269651 | A1 * | 11/2007 | Denome .............. A61K 8/0208 428/327 |
| 2008/0044480 | A1 | 2/2008 | Pommersheim |
| 2008/0107699 | A1 * | 5/2008 | Spigelman et al. .......... 424/404 |
| 2008/0131695 | A1 * | 6/2008 | Aouad .................... C11D 3/505 428/338 |
| 2008/0193761 | A1 * | 8/2008 | Naylor Rocha Gomes et al. ....... 428/402.21 |
| 2009/0009024 | A1 | 1/2009 | Draper |
| 2009/0130073 | A1 * | 5/2009 | Reindl ..................... A61K 8/99 424/93.45 |

FOREIGN PATENT DOCUMENTS

| CN | 1461734 A | 12/2003 |
| FR | 2811864 | 7/2000 |
| WO | 01/06054 | 1/2001 |
| WO | WO 0106054 A1 * | 1/2001 |
| WO | 03/059503 | 7/2003 |
| WO | WO 03059503 A1 * | 7/2003 |
| WO | 2008017962 A2 | 2/2008 |
| WO | 20081041191 | 4/2008 |
| WO | 2010/088745 | 8/2010 |

OTHER PUBLICATIONS

GB Search Report for GB Application No. GB0909909.4 dated Oct. 19, 2009.
PCT International Search Report and Written Opinion for PCT/EP2010/003377 dated Oct. 6, 2010.
Qiu, Bingi, "The Collection of Cosmetic Chemistry and Technology" Chinese Light Industry Publishing, 1st Edition, May 1997, pp. 678 and 679 (English translation provided) 4 pages.

* cited by examiner

*Primary Examiner* — Bethany P Barham
*Assistant Examiner* — Dominic Lazaro
(74) *Attorney, Agent, or Firm* — Michael Best & Friedrich LLP

(57) ABSTRACT

Microcapsules for delivery of a liquid onto a surface such as a hard surface or a textile, such as mattress ticking, are disclosed. The microcapsules have a shell with an outer face and an inner face, the inner face encapsulating the liquid, and the liquid contains a microorganism such as a beneficial microorganism in a dormant state. The outer face of the microcapsules may comprise reactive functional groups whereby the outer face is chemically bondable, for instance covalently bondable to said surface.

The microcapsules provide a beneficial microflora on said surface by rupture of the capsules deposited onto said surface to release the microorganism onto said surface. This may reduce or obviate the need for chemical antimicrobial agents to clean said surface. For surfaces which are fabrics or textiles, rupture and release may occur during use of the fabric or textile.

16 Claims, No Drawings

MICROCAPSULES CONTAINING MICROORGANISMS

INTRODUCTION

The invention relates to microcapsules containing microorganisms, such as probiotic or beneficial bacteria, and their use for deposition onto surfaces, such as hard surfaces, fabrics or textiles, to provide extended release of the microorganisms whereby a beneficial microflora may be established and maintained, discouraging colonisation of the surfaces by pathogenic or other harmful microorganisms. In particular, the invention is of use for providing a reservoir of releasable microorganisms on fabrics or textiles.

BACKGROUND

A broad range of pathogenic (=disease causing) bacteria pose numerous health problems to humans and animals. Some examples are *Clostridium difficile, E. coli, Enterococcus, Legionella, Listeria, Salmonella, Staphylococcus aureus* (MRSA) and *Streptococcus*. In addition to the dangers to individuals caused by these organisms, they are also responsible for large economic losses and costs. Using antibiotics and disinfectants, these problems were relatively easily controlled during the past decades. However, rising resistance to antibiotics and disinfectants by harmful organisms is now a problem.

Deposition of organic matter such as food spillage or vomit, faeces or urine from babies, pets and the like can result not only in soiling of the textiles such as furnishings, carpets and mattresses, but may result in lingering odour and may, in some circumstances, require the replacement of the soiled item or associated textile.

Deposition of such materials may support bacterial growth, especially in the case of faeces which already contains bacteria. This may lead to risk of disease in persons exposed to the deposits. Fungal growth, such as mould, mildew and the like may also arise. Furnishing textiles are known to contain a number of naturally occurring bacteria and other organisms. Some of these organisms may themselves give rise to odours arising from their digestion of organic matter deposits.

The use of anti-microbial chemical agents, whilst reducing the organism count associated with furnishing textiles, may give rise to concerns that some organisms may develop resistance to the chemical agents, leading to problems in the longer term.

An alternative to the use of chemical antibiotics and disinfectants has been established, using so called "friendly", or non-harmful, non-pathogenic bacteria (referred to hereinafter as beneficial bacteria). When a surface is cleaned, rather than leaving it sterile through use of strong chemical agents, beneficial bacteria are deposited onto the surface from a cleaning solution. They will consume remaining food sources, leaving neither nourishment nor space for potential pathogenic colonisers.

Because the beneficial bacteria remain active for several hours or days, the cleaning procedure only needs to be repeated after several days. Given a regular frequency of application, most pathogenic bacteria will be replaced by beneficial bacteria, giving a stable and healthy microflora on surfaces. Details of the use of beneficial bacteria for cleaning purposes may be found in US patent publication 2008107699. It is known to directly encapsulate lyophilised microorganisms such as probiotic bacteria with coatings in order to increase their viability following storage in tablets and powders for consumption.

In addition to hard surfaces, such techniques may also be used on soft surfaces such as fabrics, carpets or textiles. Here it is desirable to prevent malodour and generation of allergens. For clothing, this is achieved through regular washing, but some fabrics, such as furnishing fabrics and mattress ticking (the fabric covering mattresses) are not generally subject to washing and so are prone to colonisation by harmful microorganisms.

Although treatment by deposition of beneficial microorganisms onto surfaces is effective in preventing colonisation by harmful microorganisms in the short term, regular maintenance of the beneficial microflora is desirable, for instance by topping up the numbers of beneficial microorganisms at regular intervals.

It is desirable to reduce the need for frequent re-treatment of surfaces to give reintroduction of beneficial microorganisms, so reducing the cost and effort associated with the use of beneficial microorganisms. It is also desirable for the everyday use of a surface, hard or soft, to lead to maintenance of the beneficial microflora for longer periods than at present.

SUMMARY OF THE INVENTION

One object of the invention, amongst others, is to provide compositions and methods that may be used to establish and maintain beneficial microflora on surfaces as the surfaces are used. Another object of the invention is to provide a means for depositing beneficial microorganisms onto surfaces, particularly fabrics and textiles, such that the feel or texture of the surface is not substantially altered.

A first aspect of the invention provides a microcapsule for delivery of a liquid onto a surface by rupture, the microcapsule comprising a shell having an outer face and an inner face, the inner face encapsulating the liquid, characterised in that the liquid contains a microorganism. Suitably, the outer face of the shell of the microcapsule comprises reactive functional groups whereby the outer face is chemically bondable to said surface. In other words, the reactive functional groups are selected or adapted to form a chemical bond with a surface, such as the surface of a textile, fabric, yarn or fibre.

A second aspect of the invention provides a composition for delivery of a microorganism onto a surface comprising microcapsules according to the first aspect of the invention dispersed within a treatment solution.

A third aspect of the invention provides a method for treatment of a surface comprising:
a) providing microcapsules according to the first aspect of the invention dispersed in a treatment solution,
b) applying the treatment solution to the surface whereby microcapsules are deposited onto the surface. Preferably, the microcapsules are chemically bonded to the surface by means of functional groups on the outer face of the shell of the microcapsule, the functional groups selected or adapted to form a chemical bond, preferably a covalent bond with the surface.

A fourth aspect of the invention provides the use of microcapsules, according to the first aspect of the invention, to provide a beneficial microflora on a surface by rupture of the capsules deposited onto the surface to release the microorganism onto the surface.

DETAILED DESCRIPTION OF THE INVENTION

The microcapsule is for delivery of a liquid onto a surface by rupture, and so is suitably of a friable nature, i.e. arranged for rupture during use, subsequent to its application onto a surface. This may be arranged by choice of the strength of material making up the shell of the microcapsule and its wall thickness. The microcapsule has a shell having an outer face and an inner face, the inner face forming an enclosure for encapsulating the liquid. The liquid contains a microorganism: typically the microorganism will be in a vegetative state.

The microcapsules useful in the present invention comprise a liquid core containing the beneficial microorganism, usually in a vegetative state, and a thin polymeric shell completely surrounding the liquid core. By encapsulating the microorganism in liquid in a shell, the microorganism is protected throughout the process of application of the microcapsule to a surface. Typically the shell is of a water-insoluble material. The microorganism, when in a vegetative state, is able to withstand heat and lack of water, oxygen and the like whilst in the microcapsule. When the microcapsule is ruptured, the microorganism is brought back into a reproductive state by contact with oxygen and moisture.

The shell material surrounding the liquid core to form the microcapsule can be any suitable polymeric material which is impervious to the materials in the liquid core and the materials which may come in contact with the outer surface of the shell. The microcapsule shell wall can be composed of a wide variety of polymeric materials including gelatine, polyurethane, polyolefin, polyamide, polyester, polysaccharide, silicone resins, chitosan and epoxy resins. Many of these types of polymeric microcapsule shell materials are further described and exemplified U.S. Pat. No. 3,870,542.

Highly preferred materials for the microcapsule shell wall are aminoplast polymers comprising the reactive products of, for instance, urea or melamine and aldehyde, e.g. formaldehyde. Such materials are those which are capable of acid condition polymerization from a water-soluble prepolymer or precondensate state. Polymers formed from such precondensate materials under acid conditions are water-insoluble and can provide the requisite capsule friability characteristics to allow subsequent rupture of the capsule.

Microcapsules having the liquid cores and polymer shell walls as described above can be prepared by any conventional process which produces capsules of the requisite size, friability and water-insolubility. Generally, such methods as coacervation and interfacial polymerization can be employed in known manner to produce microcapsules of the desired characteristics. Such methods are described in U.S. Pat. Nos. 3,870,542, 3,415,758 and 3,041,288.

Microcapsules made from aminoplast polymer shell materials can be made by an interfacial polymerization process as detailed in U.S. Pat. No. 3,516,941. An aqueous solution of a precondensate (methylol urea) is formed containing from about 3% to 30% by weight of the precondensate. Water-insoluble liquid core material, such as a hydrophobic oil, is dispersed throughout this solution in the form of microscopically-sized discrete droplets. While maintaining solution temperature between 20 and 90° C., acid is then added to catalyze polymerization of the dissolved precondensate. If the solution is rapidly agitated during this polymerization step, shells of water-insoluble aminoplast polymer form around and encapsulate the dispersed droplets of liquid core material. Capsules suitable for use in the present invention may be produced by a similar method, with the beneficial bacteria dispersed through the hydrophobic liquid core material prior to polymerization. Preferably, the polymer of the shell is a melamine formaldehyde resin or includes a layer of this polymer.

Typically, the microcapsules vary in size, and may have diameters from 1 to 300 μm, preferably from 2 to 100 μm more preferably from 2 to 50 μm. The proportion by weight of shell with respect to the liquid core will typically be from 1:500 to 1:5,000. If the proportion is lower than 1:10,000 the resultant shell may be too thin. If the proportion is higher than 1:100, the resultant wall may be too strong to rupture easily. The exact details will depend upon the shell used.

The microcapsules of the present invention must be friable in nature. Friability refers to the propensity of the microcapsules to rupture or break open when subjected to direct external pressures or shear forces. For purposes of the present invention, the microcapsules utilized are "friable" if, while attached to surfaces, they may be ruptured in order to release the liquid core. For instance, if the surface is a textile or fabric, or the surface of a textile fibre or yarn, the microcapsules should rupture as a result of shear forces caused by normal handling or use.

Preferably, the outer face of the shell of the microcapsule comprises reactive functional groups whereby the outer face is chemically bondable to said surface. This enables the microcapsules to bond or to be bonded to suitable surfaces without the need for a separate adhesive composition being applied to the surface. Such adhesive compositions may alter the feel or texture of a surface. Preferably, the reactive functional group comprises a reactive moiety adapted to provide covalent bonding to said surface.

Examples of suitable reactive functional groups include groups such as acid anhydride groups, amino groups, N-substituted amino groups and their salts, epoxy groups (such as cyclohexyl epoxy groups), glycidyl groups, hydroxyl groups, isocyanate groups, urea groups, aldehyde groups, ester groups, ether groups, alkenyl groups, alkynyl groups, thiol groups, disulphide groups, silyl or silane groups, glyoxal-based groups, aziridine-based groups, groups based on active methylene compounds or other b-dicarbonyl compounds (such as 2,4-pentadione, malonic acid, acetylacetone, ethylacetone acetate, malonamide, acetoacetamide and its methyl analogues, ethyl acetoacetate and isopropyl acetoacetate), halo groups and hydrides. Polar groups (i.e. positively or negatively charged, zwitterionic or amphoteric groups) or hydrogen bonding groups may also be considered as reactive functional groups, but groups having reactive moieties providing covalent bonding are preferred.

The chemical bonds may be obtained through the introduction of functional groups in the microcapsules that bind chemically to functional groups of a surface. For instance if the surface is a fabric or a textile, the functional groups may be selected or adapted to form a chemical bond, with the fibres making up the textile or fabric, for instance with groups on the fibres such as hydroxyl groups or the like. The chemical bonds can be ionic, hydrogen bonding or, better still, covalent, where a simple chemical reaction takes place by addition or substitution. Reaction may be promoted solely by the pH of the solution in which the microcapsules are applied to the surface, normally an alkaline solution, or initiators may be included in case of an addition radical reaction. Covalent bonds are more resistant and ensure the permanence of bonding of the microcapsules to the fibres.

For surfaces with cationic charges, for example polyamide fibres when in acid conditions, negative charges may be introduced onto the outer face of the microcapsules, for instance by means of functional groups with negative charges, which will impart affinity between microcapsules and surface and provide a strong bond between the microcapsules and the fibres. Other groups, such as epoxy groups, may be incorporated into the outer face by suitable copolymerization, for instance during formation of the microcapsules.

In the case of cellulosic fibres, the process is similar to the dyeing process with reactive dyes. Just as with dyes, microcapsules should have groups, such as functional groups provided on the outer face of the shell of the microcapsules that convey affinity towards the fibres and can react with the hydroxyl groups of the cellulose.

For instance, the shell may be a melamine formaldehyde resin but with the polymerization process controlled in terms of temperature, catalyst and pH such that not all amino groups of the melamine are reacted, leaving free primary and secondary groups on the outer face of the microcapsules. This may be verified by acid-base titration.

The reactive functional groups may be introduced into the outer face of urea-formaldehyde, melamine-formaldehyde, polyamide or chitosan shells by reaction with the amino or hydroxyl groups present on the outer faces of such microcapsules.

As an alternative, microcapsules with an outer layer coating an inner polymer shell may be employed, the outer layer having suitable reactive functional groups on its outer face.

For aminoplast resins such as urea- or melamine-formaldehyde, co-monomers containing functional groups may be introduced. For instance, glycidyl methacrylate or any other suitable monomer that may contain epoxy (glycidyl) groups, or acrylic acid containing carboxylic groups may be used. Other suitable reactive functional groups are listed hereinbefore.

For microcapsules with an outer polymer layer separate from an inner structural layer, it is, for example, possible to use a shell of melamine-formaldehyde coated with a vinyl polymer, where the monomer used for forming the vinyl polymer contains a functional group that will form ionic bonds with the fibres, or groups that may react with the fibres to form covalent bonds, such as an epoxy group, alkyl with a halogen substitution, such as ethyl chloride, vinyl groups or heterocyclic groups. Other suitable reactive functional groups are listed hereinbefore.

Where the outer face is of an aminoplast resin such as urea-formaldehyde or melamine-formaldehyde, or is a polyamide or chitosan, the introduction of functional groups, such as epoxy groups or ethyl chloride, for example, may be achieved through a reaction between unreacted free amine groups and a bifunctional bridging agent (i.e. bonding agent) that contains epoxy groups, alkyl groups substituted with a halogens vinyl groups or heterocyclic, leaving the other group of the bifunctional agent free for reacting with the surface.

Further details of microcapsules with functional reactive groups for binding to surfaces, specifically to fibres, may be found in the publication WO 2006/117702. Hence, the functional reactive groups of the outer face of the shell of the microcapsules are preferably groups adapted to react with a second functional group of a surface, such as a fibre surface, whereby a covalent bond is formed between the functional reactive group of the microcapsule and the second functional group of the surface. The reactive moiety may be adapted to provide covalent bonding to the surface.

Preferably, the beneficial microorganism is selected from the group consisting of sporous bacteria, fungi, and yeasts, non-sporous bacteria, fungi and yeasts and mixtures thereof. Preferably it is a sporous bacterium. The preferred beneficial microorganisms are bacteria of the genus *Lactobacillus*. *Lactobacillus* bacteria are known and readily available to the public from various commercial suppliers. Danisco USA Inc., 3329 Agriculture Drive, Madison, Wis. 53716 is a commercial supplier of probiotic bacteria suitable for the invention. Other commercially-available strains are well-known and readily available. Bacteria may be of any suitable type, including but not limited to *Lactobacillus acidophilus, Lactobacillus plantarum, Lactobacillus salivarius, Lactobacillus delbrueckiil, Lactobacillus rhamnosus, Lactobacillus bulgaricus, Lactobacillus crispatus, Lactobacillus gasseri, Lactobacillus jensenii*; the *Lactococcus* genus including *Lactococcus lactis* (subsp. *Lactis*); *Streptococcus thermophilus; Propionibacterium freudenreichii* subsp. *Shermanii; Enterocccus* genus, including *Enterococcus faecium* and *Enterococcus thermophilus*; the *Bifidobacterium* genus, including *Bifidobacterium longum, Bifidobacterium infantis,* and *Bifidobacterium bifidum; Bacillus* genus, including *Bacillus coagulans, Bacillus thermophilus, Bacillus laterosporus, Bacillus subtilis, Bacillus megaterium, Bacillus licheniformis, Bacillus Pasteurii, Bacillus laevolacticus, Bacillus amyloliquifaciens, Bacillus mycoides, Bacillus pumilus, Bacillus lentus, Bacillus cereus* and *Bacillus circulans; Sporolactobacillus* genus; *Micromonospora* genus; *Micrococcus* genus; *Rhodococcus* genus; *Escherichia coli;* and *Pseudomonas* genus, including *Pseudomonas fluorescens* and *Pseudomonas aeruginosa*. Microorganisms broadly include bacteria, yeast or fungi. Probiotic yeast may be of any suitable type, including but not limited to the genus *Saccharomyces*, such as described in U.S. Pat. No. 6,524,575. Probiotic fungus may be of any suitable type, including but not limited to the genus *Aspergillus*, such as described in U.S. Pat. No. 6,368,591. Suitable beneficial microorganisms may be selected according to one or more particular properties. A preferred property is that the microorganisms display competitive exclusion of pathogenic organisms from the surface to which they are applied.

Some organic matter likely to be deposited on furnishing textiles and mattresses is high in fat. The beneficial organism may be selected to have high activity against fatty materials. An example of such a bacterium is *Bacillus pasteurii* which generates lipase.

The liquid used in the core of the microcapsule and in which the microorganism is contained is suitably a non-aqueous liquid, in other words containing less than 0.1% by weight of water.

Preferably, the non-aqueous liquid is a water-immiscible liquid (i.e. less than 1% solubility in water and vice versa). This assists in the formation of the microcapsules by an emulsion polymerization route. A suitable water-immiscible liquid is selected from the group consisting of organic oils, silicone oils, fluorocarbons and mixtures thereof. Silicone oils are preferred, suitably with a viscosity of 100 centistokes ($mm^2$/sec) or less, preferably 100 centistokes ($mm^2$/sec) or less at 25° C. Typically, the liquid will contain the microorganism dispersed within it. The weight percent of microorganism, expressed as a percentage of the total weight of microorganism and liquid together, will typically be from 1 to 70%, suitably from 5 to 50%.

A second aspect of the invention provides a composition for delivery of a microorganism onto a surface, the composition comprising microcapsules according to the first aspect of the invention, dispersed within a treatment solution. Preferably the treatment solution is an aqueous solution, i.e. containing at least 80%, preferably 90% or more by weight of water. This allows the surface to be dried evaporatively after treatment in order to remove the treatment solution.

Typically, the composition of the second aspect of the invention will comprise from 0.1% to 50% by weight of the microcapsules of the invention, preferably 0.2 to 30%, more preferably 0.3 to 20% depending upon how the composition is to be used. Preferably the microcapsules are stably dispersed within the treatment solution.

The composition may also comprise wetting agents such as surfactants in order to aid with the spreading of the microcapsules onto a surface to be treated. The composition may also comprise a binder (i.e. an adhesive) to assist in adhering the microcapsules to a surface. By binder is meant a compound which remains along with the microcapsules on a surface after evaporation of the rest of treatment solution has evaporated, acting as a binder layer adhering microcapsules to the surface. This binder is not the same as the bonding agent detailed hereinafter, in that it does not lead to chemical bonding of the outer face of the microcapsules to the surface, but merely adheres the microcapsules by entrapment or adhesive forces. A typical suitable binder would be, for instance, an acrylic polymer or a polyurethane resin. A suitable binder level is 0.1 to 3% by weight of the composition.

The composition of the invention may comprise a bonding agent. The bonding agent is an agent for chemically bonding the microcapsules to a surface. By a bonding agent is meant an agent that reacts to form a chemical bridge between a reactive functional group on the outer face of the microcapsules and the surface. A useful bonding agent will have two separate reactive groups as part of the molecule, one for bonding to a functional reactive group of the outer face of the shell of the microcapsule, and the other adapted to bond to groups on the surface. A preferred bonding agent is a functional trialkylsiloxane, such as 3-glicidoxypropyltrimethoxysiloxane. Such functional trialkoxysiloxanes are widely used in coupling applications in order to provide chemical bonding between polymeric matrices and textile fibres. The bridging mechanism is related to the presence of two types of reactive moieties in their structure. The bonding agent may be part of the composition of the invention, such that initial reaction with the outer face of the microcapsules takes place before the composition is applied to a surface, or the bonding agent may be applied contemporaneously with the treatment solution. When present in the composition, the bonding agent will typically be present at a level from 0.01 to 5% by weight of the composition.

The composition may be provided as a kit of parts comprising separate solutions, such as a first solution comprising the microcapsules and a second solution comprising a bonding agent, whereby the first and second solutions are combined when treating a surface.

The third aspect of the invention provides a method for treatment of a surface comprising:
a) providing microcapsules according to the first aspect of the invention dispersed in a treatment solution,
b) applying the treatment solution to the surface whereby microcapsules are deposited onto the surface.

Preferably, the microcapsules are chemically bonded to the surface by means of reactive functional groups on the outer face of the shell of the microcapsule, the reactive functional groups selected or adapted to form a chemical bond with the surface, preferably a covalent bond, for instance with a second functional group of the surface.

The method of treatment of the third aspect of the invention may be a method for controlling odour associated with deposits of organic matter on a surface.

The microcapsules can be applied by any suitable process such as padding, spraying or wiping, with the microcapsules dispersed in a liquid as set out herein. The method may be used as an industrial method, for instance to treat surfaces such as fabrics or textiles before they are incorporated into products such as furniture, mattresses, carpets and the like. In this way, the microcapsules are already present when the product is used and will help to maintain a beneficial microflora as the microcapsules rupture during normal use of the product. Alternatively, the treatment may be used as a domestic treatment by an end user of a product.

In addition to preventing or hindering colonisation by pathogenic microorganisms, the invention is also useful for preventing non-pathogenic nuisance microorganisms, such as microorganisms which may lead to discolouration or malodours on surfaces, e.g. arising from mould growth.

Where the surface is a fabric or textile, in addition to these application methods, an exhaustion method may be employed, where the fabric or textile is contacted with the treatment solution in a bath and subsequently removed with the microcapsules deposited, preferably bonded, more preferably covalently bonded, onto it. This method is particularly effective when the microcapsules are arranged to chemically bond to the surface as detailed herein.

The method of the third aspect of the invention may comprise applying a bonding agent to the surface whereby the microcapsules are chemically bonded to the surface. By a bonding agent is meant an agent that reacts to form a chemical bridge between a reactive functional group on the outer face of the microcapsules and the surface (or second functional groups of the surface). A useful bonding agent will have two separate reactive groups as part of the molecule, one for bonding to a functional reactive group of the outer face of the shell of the microcapsule, and the other adapted to bond to groups on the surface. A preferred bonding agent is a functional trialkylsiloxane, such as 3-glycidoxypropyltrimethoxysiloxane. Such functional trialkoxysiloxanes are widely used in coupling applications in order to provide chemical bonding between polymeric matrices and textile fibres. The bridging mechanism is related to the presence of two types of reactive moieties in their structure. The bonding agent is preferably applied contemporaneously with the treatment solution (i.e. the treatment solution and the binding agent are contacted with the surface within say five minutes of each other and before separation of treatment solution and surface). This enables the microcapsules to become chemically bonded to the surface to be treated without the need for a binder in the treatment composition.

After contacting the surface with the treatment solution to deposit the microparticles, the surface is preferably dried whereby treatment solution is removed and unruptured microcapsules remain chemically bonded to the surface. Where the treatment solution is aqueous, natural or forced evaporative drying may be useful. Typically, the microcapsules are applied to a surface at a level of 0.1 to 20 gram/m$^2$ of surface, preferably from 0.2 to 10, more preferably from 0.3 to 5 and even more preferably from 0.5 to 3. At these levels, there are sufficient microcapsules to give establishment and maintenance of microflora without the presence of the microcapsules leading to a major change in the appearance or texture of the surface.

After drying the surface, microcapsules are later mechanically ruptured in order to release the microorganism onto the surface. Preferably, this mechanical rupturing of the microcapsules takes place as a result of forces to which the microcapsules are subjected during the normal use of the surface. For instance, if the surface is a hard surface such as a floor, rupture may take place when people walk on the surface, so that microorganisms deposited from shoe bottoms may be countered by beneficial microorganisms released from microcapsules.

The invention is particularly of use when the surface is a textile or fabric, such as a knitted or woven fabric or a non-woven. After drying the textile or fabric, microcapsules are mechanically ruptured to release the microorganism onto the surface by shear forces generated during conventional use of the textile or fabric. Typically, larger microcapsules are more easily ruptured whereas smaller microcapsules may need greater forces to lead to rupture. It is desirable to provide polydisperse microcapsules (i.e. of various sizes).

For non-woven fabrics, it may be beneficial to incorporate the microcapsules of the invention into the liquid used for formation of the non-woven fabric such that the microcapsules are entrapped within the body of the non-woven fabric. For instance a household wiping cloth made of a non woven fabric with microcapsules of the invention entrapped therein would be useful as a cloth for wiping and cleaning hard surfaces in a kitchen or bathroom, with the microcapsules rupturing to release the microorganisms as a result of pressures and stresses as the cloth is used for wiping.

Once microcapsules containing the beneficial microorganism have been attached to fabrics being treated, it is necessary to manipulate the treated fabrics in a manner sufficient to rupture the microcapsules and thereby to release the beneficial microorganism. Microcapsules of the type utilized in the invention have friability characteristics such that the ordinary fabric manipulation which occurs when the treated fabrics are worn or used is sufficient for some of the attached microcapsules to rupture and so release the microorganism onto the fabric. A significant number of attached microcapsules can be broken by the normal forces encountered when treated garments are worn. For fabric articles which are not worn, the normal household handling operations such as folding, crumpling etc. can serve as fabric manipulation sufficient to rupture the attached microcapsules.

Where the microcapsules are chemically bonded to the fabric or textile, it may be possible to wash the fabric or textile using conventional detergents and a gentle washing protocol without rupturing or detaching some of the microcapsules. Thus the microcapsules may still be present after washing in order to provide a desired microflora on rupture.

For instance, the invention may be used to provide a mattress ticking upon which are deposited the microcapsules of the invention. The microcapsules may be applied by an industrial process to the ticking prior to making it up into a mattress cover, or after the mattress has been formed, or may be applied to the mattress ticking in a domestic situation, for instance by an end user or a treatment provider. In use, when the mattress is slept on, the movement of a body may rupture microcapsules deposited on or in the ticking leading to release of the liquid from the microcapsules and release of the beneficial microorganism from its vegetative state. This allows the microflora of the mattress ticking to be maintained in a beneficial state, with topping up of the beneficial microflora taking place when the mattress is used.

Once released and activated (for instance by contact with moisture), the beneficial organisms may grow and replicate, consuming organic matter in any deposit on a surface until the matter is consumed. After the matter has been consumed, the organisms may again become dormant, for instance by spore formation.

It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

The invention claimed is:

1. A composition comprising a microorganism within unruptured microcapsules, the composition comprising:

friable microcapsules having a diameter from 1 to 300 μm in a concentration of from 0.1% to 50% by weight of the composition dispersed within an aqueous treatment solution, the microcapsules being present in the composition in an amount for the microcapsules to be applied at a level of 0.1 to 20 gram/$m^2$ when applied to a textile surface, the microcapsules adapted for delivery of a liquid onto the textile by rupture during conventional use of said textile, the microcapsules comprising a shell encapsulating the liquid to form a liquid core, the liquid containing a microorganism that consumes organic matter deposited on the textile surface;

wherein said microorganism is in a vegetative state, and is brought back into a reproductive state by contact with oxygen and moisture upon the rupture of the microcapsule.

2. The composition of claim 1 wherein outer faces of the microcapsules comprise reactive functional groups whereby the outer faces are chemically bondable to said textile.

3. The composition of claim 2 wherein the reactive functional group comprises a reactive moiety adapted to provide covalent bonding to said textile.

4. The composition of claim 1 wherein the microorganism is selected from the group consisting of sporous bacteria, sporous fungi, non-sporous bacteria, non-sporous fungi, and mixtures thereof.

5. The composition of claim 4 wherein the microorganism is a sporous bacterium.

6. The composition of claim 5 wherein the liquid is a non-aqueous liquid comprising less than 0.1% by weight water.

7. The composition of claim 6 wherein the non-aqueous liquid is a water-immiscible liquid.

8. The composition of claim 7 wherein the water-immiscible liquid is selected from the group consisting of organic oils, silicone oils, fluorocarbons and mixtures thereof.

9. The composition of claim 1 wherein the shell comprises a polymer layer, the polymer selected from the group consisting of gelatines, polyurethanes, polyolefins, polyamides, polyesters, polysaccharides, silicone resins, epoxy resins, chitosan and aminoplast resins.

10. The composition of claim 9 wherein the polymer is a melamine formaldehyde resin.

11. The composition of claim 1 wherein the shell comprises a polymeric material surrounding the liquid core which is impervious to the materials in the liquid core.

12. The composition of claim 1 wherein the proportion by weight of shell relative to the liquid core in said microcapsules is from 1:500 to 1:5,000.

13. The composition of claim 1 wherein the microcapsules are adapted for delivery of said liquid onto said textile surface by rupture resulting from movement of a body on the textile.

14. The composition of claim 1, whereby the microorganism reduces a concentration of allergens on the textile surface.

15. The composition of claim 1 wherein the textile comprises a ticking material of a mattress.

16. The composition of claim 1 wherein the microorganism is selected from the genus *Bacillus*.

* * * * *